United States Patent [19]

Santucci et al.

[11] Patent Number: 4,512,743

[45] Date of Patent: Apr. 23, 1985

[54] METHOD FOR MASKING DISCOLORATION ON TEETH

[75] Inventors: Edward A. Santucci, Plainsboro; William B. Racz, Milltown, both of N.J.

[73] Assignee: Johnson & Johnson Dental Products Company, East Windsor, N.J.

[21] Appl. No.: 346,348

[22] Filed: Feb. 5, 1982

[51] Int. Cl.³ .............................................. A61K 6/08
[52] U.S. Cl. .................................... 433/217; 106/35; 523/115; 523/118
[58] Field of Search ................ 433/217; 523/115, 118; 106/35

[56] References Cited

U.S. PATENT DOCUMENTS

| | | | |
|---|---|---|---|
| 4,010,545 | 3/1977 | Kilian et al. | 523/105 |
| 4,131,729 | 12/1978 | Schmitt et al. | 523/116 |
| 4,150,485 | 4/1979 | Lee et al. | 433/217 |
| 4,411,625 | 10/1983 | Koblitz et al. | 433/217 |

Primary Examiner—Lorenzo B. Hayes
Attorney, Agent, or Firm—Charles J. Metz

[57] ABSTRACT

A polymerizable composition comprising liquid polymerizable acrylic monomer, a polymerization initiator for the monomer, sub-micron silica, and pigments, is employed as a dental veneer to mask tooth discoloration.

3 Claims, No Drawings

METHOD FOR MASKING DISCOLORATION ON TEETH

The invention relates to a process for applying a coating to the surface of a tooth to hide discoloration and other similar imperfections.

BACKGROUND OF THE INVENTION

There is a clear need in the dental profession for an inexpensive and effective means for the cosmetic treatment of discolored teeth. Discoloration can result from many different causes, such as nicotine staining, excessive ingestion of fluoride, reaction to tetracycline and similar pharmaceutical products, trauma, root canal therapy, and various systemic disorders.

Discolored teeth are treated by dentists in a number of different ways short of extraction. Bleaching has been tried, but the results are unpredictable. Sometimes it doesn't help at all, and in any case, it is difficult to control the final color of bleached teeth. Crowns ("capping") have also been used. But crowns are quite expensive and require considerable grinding away of the tooth. Further, they are usually contraindicated with children.

Polymerizable dental composite materials have been used to treat discolored teeth in the following manner:

Peroxide-cured, filled polymeric materials are shaped by placement in the anterior portion of a plastic crown former, which acts as a mold. The material is then applied to the tooth, using a layer of unfilled bonding agent as a "primer coat" on the tooth. After the material has hardened, it must be polished. Cured resin-filled, composite polymeric materials have been used in a similar manner, except that the crown former was not used as a mold. But the dentist still had to shape it by hand and polish the veneer. (See Spencer, J. Dent. Child, 39, pp. 443–446, November-December, 1972.)

Preformed veneers can also be used. They are applied by using unfilled bonding agents to adhere the veneer to the tooth and filled composites to "feather" the corners.

None of the above-discussed known procedures for treating discolored teeth is fully satisfactory. Crowns are expensive; bleaching is unpredictable; the use of polymeric composites requires an awkward procedure; and preformed veneers are bulky, require time-consuming and complicated procedures to install, tend to leak around the margins, and can't be shaded.

The present invention provides a relatively inexpensive and effective means for treating discolored teeth.

BRIEF SUMMARY OF THE INVENTION

The invention provides a process which comprises the steps of:
(a) removing surface film, when necessary, by cleaning the tooth to be treated;
(b) etching the tooth surface with an etching composition (which is described below);
(c) cleaning the etched surface to remove the etching composition and debris;
(d) drying the etched tooth surface; and
(e) coating the dry etched tooth surface directly with a polymerizable composition comprising a liquid polymerizable acrylic ester monomer, a polymerization initiator for said monomer, sub-micron silica filler, and pigments appropriate to match the appearance of the natural tooth.

The above-mentioned polymerizable composition has the following desirable combination of properties, which account for its successful use in the method of the invention:

(1) It is easy to work with and use in that it can be formulated to have a convenient working time, and when applied to the tooth, it has good film-forming or leveling properties and does not run, slump, or sag;
(2) When cured, the film has excellent adhesion to the tooth and has good wearing properties so that the film will last for a reasonable period of time, e.g., for about two years or more;
(3) The cured film has good hiding power and is effective in masking discoloration and other defects in a very thin layer, in some cases as thin as ¼-millimeter;
(4) The cured film bears a close resemblance to natural tooth enamel;
(5) The polymerizable composition is relatively inexpensive and can be applied by a simple, straightforward procedure, thereby making the process of the invention a much less expensive way to effect cosmetic improvement of the teeth when compared with alternative procedures such as capping;
(6) The composition is applied directly to the tooth without the need to use a primer or bonding coat. The fact that it can be used without a primer coat results in at least two advantages. First, the total thickness of the veneer can be less, and second, a layer of different material, which might have a different coefficient of thermal expansion than the top veneer coat, is eliminated;
(7) The cured veneer of the invention requires minimal polishing, and in many cases, no polishing at all is needed;
(8) The composition is quite versatile in that a wide range of colors and degrees of opacity can be obtained; and
(9) The composition can be used to "characterize" the tooth. That is, the tooth can be given different shades and/or degrees of opacity in different locations, to mimic the characteristics of natural enamel.

THE PRIOR ART

Unfilled acrylic ester monomer compositions have been used as a surface glaze to finish composite restorations.

Unfilled acrylic ester monomer compositions have been used as pit and fissure sealants on the occlusive surfaces of molars in order to retard caries formation. In this respect, see Kemper, U.S. Pat. No. 4,261,879 and British Pat. No. 1,557,263, issued Feb. 6, 1980.

Acrylic ester monomer compositions containing fumed silica filler have been used as orthodontic bracket adhesives. See Kilian et al., U.S. Pat. No. 4,010,545.

Acrylic ester monomer compositions containing microfine silica filler have been disclosed as being useful as dental materials in Australian Pat. No. 77,413/75. The patentees define "dental materials" as "fillings for cavities, fixing cements, sealing and protective coatings, crown and bridge materials, and denture base materials and substances for manufacturing artificial teeth based on polymerizable monomers and/or polymers". The bulk of the patent's disclosure relates to artificial teeth or parts of teeth, denture base material, and filling material.

DETAILED DESCRIPTION OF THE INVENTION

The tooth surface to be treated in accordance with the invention must be clean so that no significant amounts of plaque, calculus, surface film or pellicle, or the like are present. Cleaning can be done by known procedures.

The clean tooth surface is then etched by applying thereto a suitable known etching solution such as 35–50 weight percent aqueous phosphoric acid. The etching solution is left in contact with the tooth surface for the usual period of time, e.g., about one minute, and is then rinsed with water. The tooth surface is then dried.

The polymerizable composition is then applied to the tooth and allowed to harden. It can be painted or daubed on with a brush in one or more layers. If desired, the first layer can be quite opaque to mask discoloration, with a second layer being more translucent to more closely resemble natural tooth enamel. Usually, a total thickness of one-half to one millimeter will be used, although thinner or thicker coatings can be used in appropriate cases.

Only minimal polishing, if any, is required for the cured veneers of the invention. Conventional polishing procedures can be used.

A preferred polymerizable composition for use in the invention is a peroxide-catalyzed liquid difunctional acrylic ester composition comprising BIS-GMA, triethylene glycol dimethacrylate (TEGDM), fumed silica, pigments, a peroxide catalyst, and an accelerator for said catalyst. This composition has good surface cure and tenacious longterm retention on the tooth. The difunctional acrylic esters that contain two polymerizable groups are preferred because such esters exhibit a lesser degree of shrinkage during polymerization than the monofunctional acrylics.

The monomer BIS-GMA is the diglycidyl dimethacrylate derivative of bisphenol-A; more precisely: 2,2-bis[4-(3-methacryloxy-2-hydroxypropoxy)phenyl]propane.

There may further be included in the composition the monomer bisphenol-A dimethacrylate (BADM), preferably up to about three parts by weight BADM for every nine parts BIS-GMA, and more preferably about one part by weight BADM for every nine parts BIS-GMA. Other known monomers that are suitable for use in dental composites may also be employed.

The preferred acrylic ester compositions of the invention have a working time of about 120 seconds. Thus, the identity and amounts of peroxide catalyst, amine accelerator, and stabilizer (if any) are adjusted to achieve the desired working time. If stabilizers are added, the amounts of accelerator and catalyst may be increased to maintain the desired set time. The known accelerators may be used. The preferred accelerators are N,N-dialkylanilines such as N,N-bis(2-hydroxyethyl)-4-methylaniline and N,N-bis(2-hydroxyethyl)-3,4-dimethylaniline.

While the preferred peroxide catalyst for the compositions of the invention is benzoyl peroxide, other peroxide catalysts may be employed.

A light-activated system utilizing known photoinitiators, activators, etc., can be used, if desired.

Stabilizers may be added to the material, if desired, to inhibit premature polymerization during storage, or to adjust the set time, or to stabilize the color of the cured veneer. Such stabilizers are generally free-radical chain reaction terminators such as substituted phenols, exemplified by p-methoxyphenol, 2,5-di-t-butyl-4-methylphenol (known as BHT), pentaerythritol tetrakis [3-(3,5-di-t-butyl-4-hydroxyphenyl)propionate] (sold by Geigy Chemical Company under the name Irganox 1010), ultraviolet screens such as 2-hydroxy-4-methoxy benzophenone, and the like.

The polymerizable composition also contains submicron silica, such as fumed silica. Sub-micron silica has a median particle size below one micron. Fumed silica, the preferred sub-micron silica, has a maximum particle size of about 0.05 micron. The silica is preferably silane treated in order to ehnance its adhesion to the cured resin. Such materials are known and are commercially available as, for instance, "AEROSIL" 972 by Degussa Corporation and silane treated CAB-O-SIL by the Cabot Corporation.

The sub-micron silica is used in a proportion sufficient to impart the desired viscosity characteristics to the polymerizable composition. It is required that the composition be made to level, i.e., form a smooth surface without polishing, and yet not slump or run. Usually the desired viscosity which will yield the desired balance of levelling and slump properties will be found within the range of from about 100,000 to 300,000 centipoises (tested as discussed below in the examples). However, acceptable viscosities may be found outside that range, in some cases, depending on variables such as nature of resin system and nature and average particle size of the filler.

When fumed silica is the sole filler, the proportion used to achieve the desired viscosity characteristics will usually be found within the range of about 7 to 14 weight percent, based on total weight of the polymerizable composition. When other submicron silicas are used in lieu of or in addition to fumed silica, the proportions may vary. In particular, with slightly larger sized fillers (such as sub-micron quartz), larger proportions of filler may be used.

As was mentioned above, the filler is a sub-micron silica having a median particle size below one micron. The maximum particle size permitted is that which will not adversely affect the self-polishing characteristics of the veneer. Usually the maximum particle size is about 2 or 3 microns, although this is dependent upon factors such as proportion of the larger particles, and the like.

The polymerizable composition also contains a small proportion of pigments in order to match the appearance of natural teeth. Such pigments include titanium dioxide and iron oxides.

The above-described composition is preferably prepared as two separate compositions, one containing catalyst and no accelerator, and the other containing accelerator and no catalyst. Each of these materials would preferably contain the identical quantity of polymerizable monomer(s), but would vary only in the presence of the peroxide or amine accelerator and amount of stabilizer. These two separate compositions may then be combined to yield the polymerizable compositions of the invention, which is then applied to the tooth.

The practice of the present invention is further illustrated by the following Example, which is given for purposes of illustration only and not to limit the invention thereto. All parts are by weight unless otherwise noted.

EXAMPLE 1

Two compositions were prepared by mixing the following ingredients:

TABLE I

|  | Universal | Catalyst |
|---|---|---|
| 90:10 BIS—GMA:BADM | 70.00 | 70.00 |
| TEGDM | 30.00 | 30.00 |
| 2-hydroxy-4-methoxy benzophenone | 1.00 | 1.00 |
| BHT (Stabilizer) | 0.05 | 0.15 |
| benzoyl peroxide | — | 2.00 |
| N,N—bis(2-hydroxyethyl)-4-methylaniline | 3.00 | — |
| AEROSIL R972 Fumed Silica | 12 | 12 |

The various colored formulations are illustrated by the following:

TABLE II

| | Color Concentrate Formulations | | | |
|---|---|---|---|---|
| | Red | Yellow | Black | Brown |
| Base Formulation, Universal | 100.00 | 100.00 | 100.00 | 100.00 |
| Iron Oxide (Pur Oxy Red) | 1.00 | — | — | — |
| Iron Oxide (Pur Oxy Yellow) | — | 1.00 | — | — |
| Iron Oxide (Pur Oxy Black) | — | — | 1.00 | — |
| Iron Oxide (Pur Oxy Brown) | — | — | — | 1.00 |

TABLE III

| | UNIVERSAL FORMULATIONS | | | | | | |
|---|---|---|---|---|---|---|---|
| | White | Red | Yellow | Black | Brown | Opaque | Clear |
| Base Formulation Universal | 100.00 | 100.00 | 100.00 | 100.00 | 100.00 | 100.00 | 100.00 |
| Red Color Concentrate | — | 5.00 | — | — | — | — | — |
| Yellow Color Concentrate | — | — | 5.00 | — | — | 1.00 | — |
| Black Color Concentrate | — | — | — | 5.00 | — | — | — |
| Brown Color Concentrate | — | — | — | — | 5.00 | 1.50 | — |
| $TiO_2$ | 2.00 | — | — | — | — | 2.00 | — |

This material was used to veneer the entire labial surface of six upper incisor teeth in three patients. The veneer was applied by painting on with a brush, after the surfaces to be veneered were etched, cleaned, and dried.

Indications for this procedure included the following:
1. Discolored teeth due to root canal therapy.
2. Existing discolored Class IV restorations.
3. Discolored teeth due to existing lingual cast gold veneers.

The formulation handled well clinically in that it flowed sufficiently to produce a smooth surface and yet did not slump. This allowed for a relatively quick veneering procedure.

The bulk of the resulting veneer required no finishing or polishing. The surface was smooth and lustrous. Minimal finishing is required at the gingival and interproximal margins to remove excess material.

The veneers were successful in masking underlying discolorations and defects even though the material did not exceed 1.5 millimeters in thickness. The esthetic improvement for these teeth was dramatic as they were more in harmony with remaining dentition.

EXAMPLE 2

The universal formulation described above in Example 1 had a viscosity of 285,000 centiposes, tested at 24°±1° C., using a Brookfield Viscometer with an "E" cross bar spindle and a Model D helipath stand.

What is claimed is:
1. A method for masking discoloration on a tooth comprising the steps of:
   (a) etching the surface of a tooth to be treated with an etching composition, said surface being substantially free of surface film;
   (b) cleaning the etched tooth surface to remove the etching composition and debris;
   (c) drying the etched tooth surface; and
   (d) coating the dry etched tooth surface with a polymerizable composition having a viscosity at 24°+1° C. of 100,000 to 300,000 centipoises, said polymerizable composition comprising liquid polymerizable acrylic ester monomer, a polymerization initiator for said monomer, sub-micron silica filler, and a color concentrate containing pigments appropriate to match the appearance of the natural tooth enamel, the proportion of said filler being selected so as to impart levelling and nonslump properties to said polymerizable composition.
2. The method of claim 1 wherein said liquid polymerizable acrylic ester monomer comprises bis-GMA, bisphenol-A dimethyacrylate, and triethylene glycol dimethacrylate.
3. The method of claim 1 or 2 wherein said submicron silica is fumed silica.

* * * * *